United States Patent [19]
Elliott

[11] Patent Number: 5,938,590
[45] Date of Patent: Aug. 17, 1999

[54] OTOSCOPE RETROFIT KIT TO ALLOW MULTIPURPOSE USE

[76] Inventor: Peter Christopher Elliott, No. 2 Lakeside, Austin, Tex. 78746

[21] Appl. No.: 09/080,894
[22] Filed: May 18, 1998
[51] Int. Cl.⁶ .................................................. A61B 1/227
[52] U.S. Cl. ........................... 600/184; 600/200; 606/162
[58] Field of Search ................................... 600/184, 200; 606/106, 162

[56] References Cited

U.S. PATENT DOCUMENTS

| | | | |
|---|---|---|---|
| 1,693,021 | 11/1928 | Cameron | 600/200 |
| 2,039,546 | 5/1936 | McGerry | 600/200 |
| 3,146,775 | 9/1964 | Moore et al. | 600/200 |
| 3,596,653 | 8/1971 | Hotchkiss | 600/200 |
| 3,812,847 | 5/1974 | Moore et al. | 600/200 |
| 3,958,566 | 5/1976 | Furihata . | |
| 4,006,738 | 2/1977 | Moore et al. . | |
| 4,380,998 | 4/1983 | Kieffer, II et al. . | |
| 5,209,219 | 5/1993 | Hollobaugh . | |
| 5,390,663 | 2/1995 | Schaefer . | |
| 5,454,817 | 10/1995 | Kotz . | |

FOREIGN PATENT DOCUMENTS 2566668  1/1986  France ..................................... 600/200

*Primary Examiner*—Jeffrey A. Smith
*Attorney, Agent, or Firm*—Joseph F. Long

[57] ABSTRACT

A removable Tee piece to allow connecting to a vacuum source to pull a vacuum in the interior of an otoscope and to allow finger pressure control of the interior vacuum and a plastic foreign body remover extension of the speculum holder of the otoscope allows insertion of the otoscope for removal of foreign bodies from an ear or a nose by using the vacuum to pull and hold a foreign body against the extension as the otoscope is withdrawn. A speculum holder modified to prevent the speculum from making a seal with the outer ear and differing embodiments of the foreign body remover extension are shown. In all instances the retrofitted unit is prevented from making an outer ear seal. Removal of the Tee piece and extension of the speculum holder retrofit units allows the normal use of the otoscope for an ear inspection.

3 Claims, 3 Drawing Sheets

OTOSCOPE RETROFIT KIT TO ALLOW MULTIPURPOSE USE

BACKGROUND

An otoscope is an instrument normally designed to allow a physician to peer inside an ear or into a nose through a lighted pathway and to allow directing wash liquid inside an ear or nose through an insufflation port. At times, particularly in infants, there are foreign bodies such as a bead within an ear or nose that necessitate removal. A better method than insufflation for foreign body removal is desirable and at times is a necessity.

The objectives of this invention include low cost retrofitting of an otoscope to allow removal of foreign material from a nose and ear in a rapid patient comfortable manner.

The invention includes a Tee piece with one arm of the Tee sized to snap into the insufflation port of the otoscope; a second arm to connect to a vacuum source and a third arm open to the atmosphere to be partially closed using finger pressure in order to allow the user to have a control over the vacuum in the otoscope. The size of the finger closable arm opening and control of the vacuum source are such that with the finger closable arm totally open there is essentially no vacuum in the otoscope.

The invention further includes several embodiments of retrofitting units for the speculum of the otoscope to allow the user to operably attach one of the retrofit units on the speculum or on the speculum holder and insert the otoscope to place the end of the retrofit unit lightly against a foreign body and to partially close the atmospheric end of the Tee piece to pull a slight vacuum to hold the foreign body against the end of the retrofit unit thereby allowing removal of the foreign body by withdrawing the otoscope. In all embodiments the speculum or the foreign body remover extensions are ridged or so formed as to prevent in use sealing of the retrofitted speculum or speculum holder against the outer ear to thereby form a cavity wherein a slight vacuum could damage the tympanic membrane.

Minor changes to the speculum or the speculum retrofit units of the otoscope would be easily made but would be within the purview of the invention. We wish to be limited only to the spirit and purpose as outlined in these specifications and claims.

SUMMARY OF THE INVENTION

The invention encompasses simple low cost removable additions or retrofit units to allow use of a vacuum source and a users thumb or finger pressure to adjustably pull a slight vacuum in the interior of an otoscope without interfering with the users line of sight to inspect an interior of an ear or a nose. When a foreign body is detected in an ear or nose a modified speculum or a removable throw away type foreign body remover extension to the end of the speculum or the end of the speculum holder of the otoscope is installed to allow placing the distal end of the remover extension close to the foreign body and using a slight vacuum to hold the foreign body against the remover extension unit thereby allowing easy painless removal by simply disengaging the otoscope. The Tee piece is preferably made of a heat sterilizable semi-rigid plastic with one arm of the Tee piece sized to removably snap into the insufflation port of the otoscope and a second arm with a smooth larger opening to facilitate finger or thumb closure. The remaining arm is preferably ridged to fit firmly into a tubing leading to a vacuum source.

In all embodiments the modified speculum or the foreign body remover extensions are ridged or so formed as to prevent in use sealing of the retrofitted speculum against the outer ear to thereby form a cavity wherein a slight vacuum could damage the tympanic membrane.

The distal end of foreign body remover extension units when installed on the speculum or speculum holder may be chosen to extend from about one half to an inch and one half past the end of the speculum depending upon the intended use in an ear or a nose.

DESCRIPTION OF THE INVENTION

Figure 1:
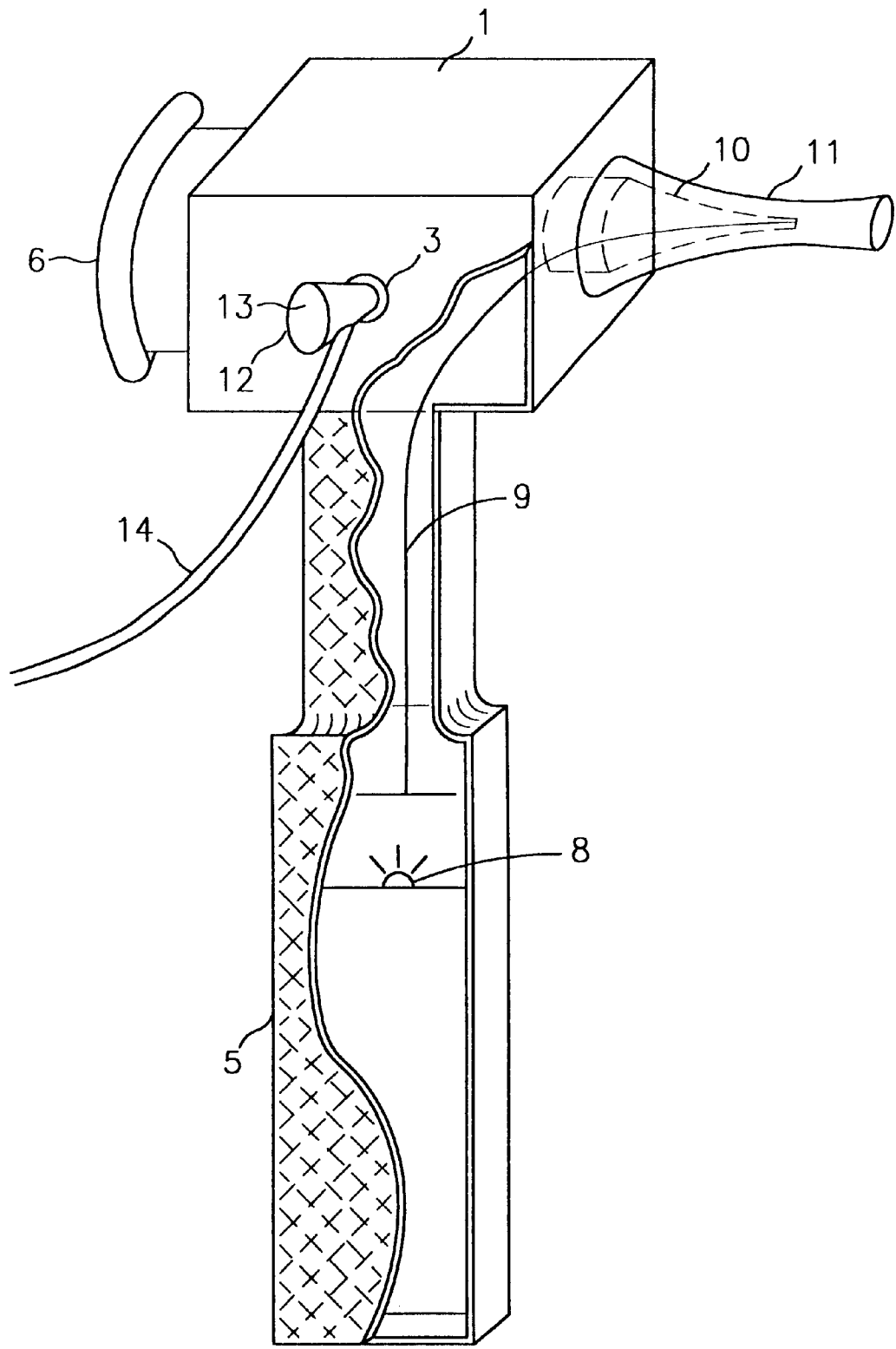
FIG. 1 shows an otoscope with retrofit units in place to allow multipurpose use.
Figure 2:
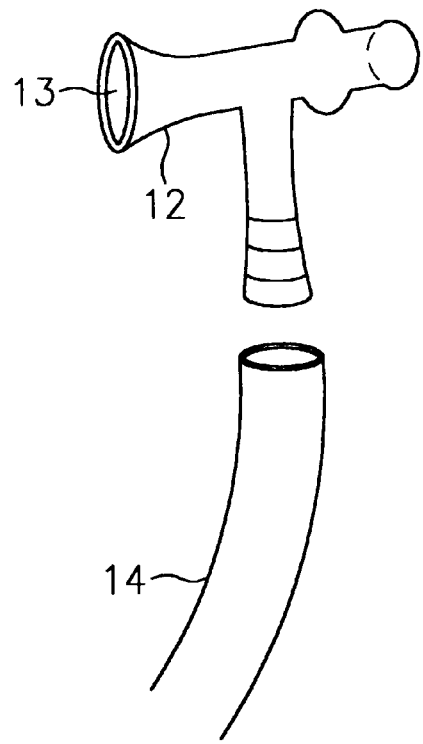
FIG. 2 shows a Tee piece to allow adjustably pulling a vacuum inside the otoscope.
Figure 3:
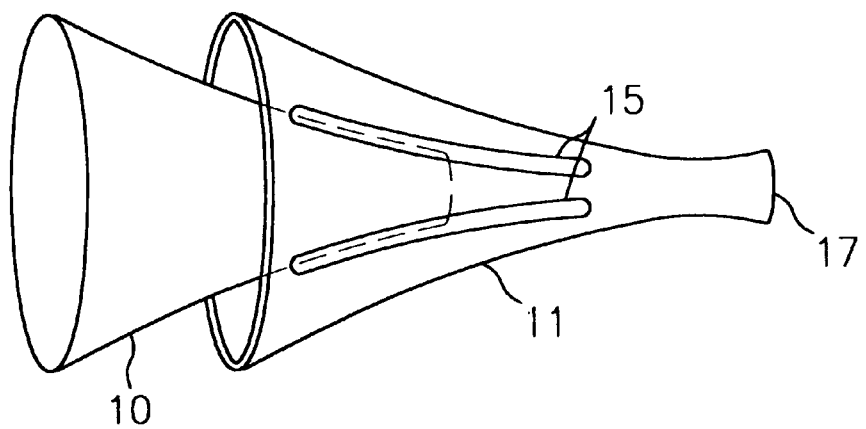
FIG. 3 shows a modified speculum retrofit unit for a foreign body remover.

The invention may best be described from the drawings. In FIG. 1 an otoscope 1 head with handle 5 is shown. An electrically powered light 8 with a fiber optic bundle 9 furnishes light to the distal end or tip of the cone shaped speculum holder 10; with speculum 11 in place a viewer may inspect an interior of an ear by looking through lens 6. The tip of the speculum is about one eighth of an inch in diameter. One embodiment of a ribbed speculum to act as a foreign body remover is shown in FIG. 3. The Tee shaped vacuum connector piece 12, FIG. 1, shown in more detail in FIG. 2, is shown snapped in place in the insufflation port 3 and connected to a vacuum source through flexible line 14. In hospitals the house vacuum could be used but low cost, low volume light weight diaphragm pumps are readily available. With both the vacuum connector unit 12 and the ribbed speculum 11 in place a physician user may place the flared tip 17, FIG. 3, against the foreign body in the ear or nose and partially close opening 13 of the vacuum connector unit 12 with thumb or finger pressure to pull the foreign body against the tip 17 thereby allowing removal of the foreign body by simply withdrawing the otoscope while continuing to hold the vacuum in the otoscope.

Varying the pressure within the otoscope allows a Physician to cause the tympanic membrane within an ear to vibrate to determine if there is fluid behind the tympanic membrane.

In FIG. 2 the Tee shaped vacuum connector 12 may be made of any one of several semi-rigid plastics with a heat sterilizable plastic being preferred. Opening 13 is preferably slightly flared to aid in closure by thumb or finger pressure. Both other arms of the unit 12 may be ribbed or ridged to allow the straight through snap in arm to hold more solidly in place in the insufflation port and to allow the Tee arm to hold more firmly to the tubing 14. Depending on the vacuum source used a needle valve adjustment, not shown, may be necessary in line 14 so that with opening 13 totally open there would no vacuum in the interior of the otoscope even though the vacuum source is fully connected and activated.

FIG. 3 shows the ribbed speculum 11 with flared tip 17 that fits over speculum holder 10 that is an integral part of the otoscope and has a lighted tip as shown in FIG. 1. One or more ribs 15 that are a minimum of about one millimeter in height are necessary to prevent the otoscope when in use from forming a seal in the outer ear thereby creating a cavity above the tympanic membrane. The rib or ribs 15 form a vent to the atmosphere to prevent a slight vacuum from injuring the tympanic membrane. The ribs start about one half inch from the tip and extend essentially the full length of the speculum. The flared distal end 17 of unit 11 extends outward from the end of the speculum holder 10 about one half inch for use in an ear and about one inch for nasal use.

Figure 4:
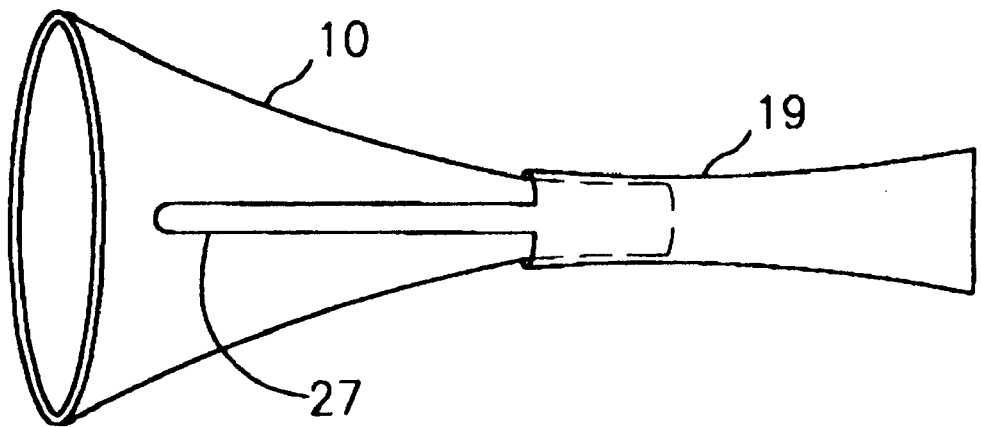
FIG. 4 shows an embodiment of a speculum holder retrofit unit wherein an extended rib from the retrofit unit acts as vent.

FIG. 4 shows and embodiment of the foreign body remover, 19 stretchably held on to the speculum holder 10. The unit 19 is a straight section of stretchable plastic tubing about one to one and one half inches long with a flared end to grab or hold a foreign body when the flared end is held against a foreign body and a vacuum is pulled in the interior of the otoscope. An integral riblike extension 27 allows atmospheric venting and prevents the otoscope from forming a seal in the outer ear.

Figure 5:
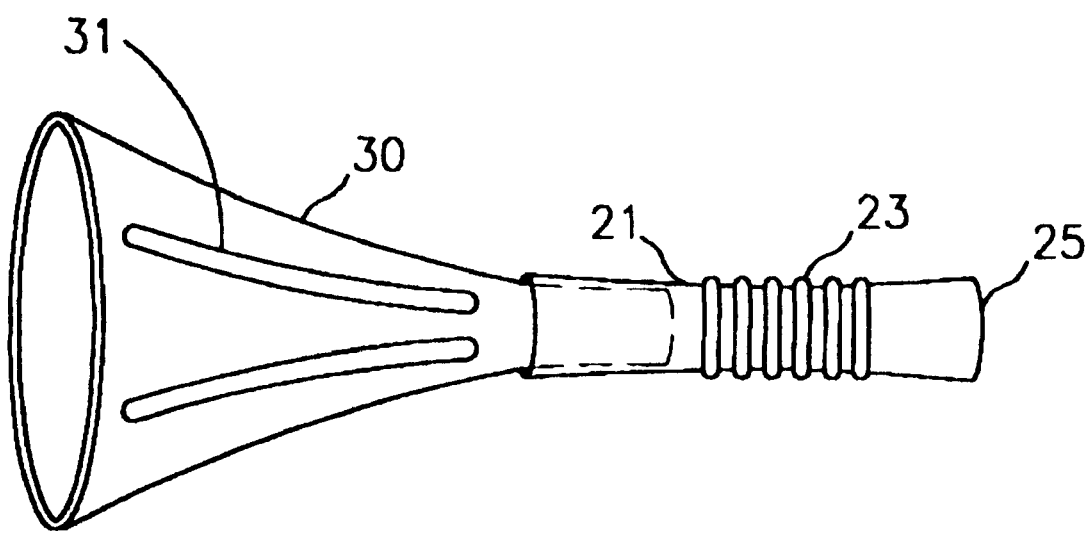
FIG. 5 shows a third embodiment of a speculum retrofit unit and a modified ribbed speculum.

FIG. 5 shows a speculum modified by having one or more vent ribs that may integrally formed or glued to a normal smooth cone shaped speculum. The ribs 31 on the modified speculum 30 are a minimum of one millimeter high and may be less than one eighth inch wide. FIG. 5 also shows another embodiment 21 of a foreign body remover retrofit unit. This unit uses corrugations 23 that are similar to those found in the widely used bendable soda straws. After the user locates the foreign body some bending may be required to fit the flared end 25 over the foreign body. The corrugations allow bending without collapsing the plastic tube forming the unit. The retrofit unit 21 could have an extension similar to 27, FIG. 4 and then would be usable over a speculum holder 10 as shown in FIG. 4.

What is claimed is:

1. A retrofit kit to allow mutipurpose use of an otoscope comprising:
    a) T shaped vacuum connector means with a first end operably connectable to an interior of said otoscope through an insufflation port of said otoscope; with a second end operably connectable with an exterior vacuum source; and with a third end open to the atmosphere and shaped to allow finger pressure closure; variation of said finger pressure closure allowing a user to vibrate a tympanic membrane within an ear to determine excess fluid behind said tympanic membrane;
    b) a first semi-flexible, ribbed, cone shaped speculum means fittable on a speculum holder on said otoscope; said ribbed, cone shaped speculum means having a lighted line of sight through said cone shaped means and having a flared soft plastic distal end extending past a distal end of said speculum holder and acting to hold a foreign object to allow removal when a user uses said finger pressure closure on said T shaped connector means to pull a slight vacuum in said otoscope; said ribs on said ribbed, cone shaped speculum means act to prevent said ribbed speculum means from forming an outer ear seal, said ribs thereby acting as an atmospheric vent to prevent a slight vacuum from injuring said tympanic membrane.

2. A retrofit kit to allow multipurpose use for an otoscope as in claim 1 wherein a second semi-flexible plastic foreign body remover retrofit means may be used to replace said first semi-flexible ribbed cone shaped speculum means and is formed from a straight tube, has a flared distal end, and a beginning end that is stretchably fittable over a beginning end of said speculum holder and has a riblike extension means on said beginning end that acts to prevent said retrofitted speculum holder from forming an outer ear seal when said retrofitted otoscope is inserted in an ear.

3. A retrofit kit to allow a multipurpose use for an otoscope comprising:
    a) a T shaped vacuum connector means with a first end operably connectable to an interior of said otoscope through an insufflation port of said otoscope; with a second end operably connectable with an exterior vacuum source; and with a third end open to the atmosphere and shaped to allow finger pressure closure, variation of said finger pressure closure allowing a user to vibrate a tympanic membrane within an ear to determine excess fluid behind said tympanic membrane;
    b) a rib means on an exterior surface of a cone shaped speculum for said otoscope, a beginning end of said rib means starting about one half inch back from a smaller end of said speculum, extending back to a beginning end of said speculum and acting to allow atmospheric venting to a space above said tympanic membrane of said ear,
    c) a foreign body remover extension means for said speculum of said otoscope, said extension means being an open tube with a flared distal end and having tube corrugations to facilitate bending adjacent to said flared distal end and a stretchable beginning end sized to be stretchably connectable on a small end of said speculum and to allow a user, through a lighted line of sight to locate a foreign body and to allow said extension means to hold said foreign body against said flared distal end to allow removal of said foreign body by disengaging said otoscope after said flared distal end of said extension means is placed lightly against said foreign body and finger pressure on said third open end of said T shaped vacuum connector means adjustably pulls a vacuum in said speculum and said foreign body remover extension means to hold said foreign body against said flared distal end of said foreign body remover extension means.

\* \* \* \* \*